United States Patent [19]

Ideguchi et al.

[11] Patent Number: 5,250,068
[45] Date of Patent: Oct. 5, 1993

[54] OPTICAL TRANSMISSION TYPE ACUPUNCTURE NEEDLE

[75] Inventors: Emuko Ideguchi, Shinjyuku; Shuji Yamada, Koube, both of Japan

[73] Assignee: Yakuouji Shinkiyu Chiryouin, Japan

[21] Appl. No.: 11,095

[22] Filed: Jan. 29, 1993

Related U.S. Application Data

[63] Continuation of Ser. No. 800,097, Nov. 29, 1991, abandoned.

[30] Foreign Application Priority Data

Nov. 30, 1990 [JP] Japan ................................. 2-330516

[51] Int. Cl.$^5$ ............................................. H04C 00/00
[52] U.S. Cl. ....................................... 606/189; 606/13; 606/185; 128/907
[58] Field of Search ........................ 606/189, 13, 185; 128/907

[56] References Cited

U.S. PATENT DOCUMENTS 3,943,932 3/1976 Woo ................................. 128/907 X
4,535,784 8/1985 Rohlicek et al. ............... 128/907 X

FOREIGN PATENT DOCUMENTS 2740969 3/1979 Fed. Rep. of Germany ...... 128/907

Primary Examiner—Randall L. Green
Assistant Examiner—Dinh X. Nguyen
Attorney, Agent, or Firm—Evenson, McKeown, Edwards & Lenahan

[57] ABSTRACT

An acupuncture needle for treating diseased parts in a patient's body by sticking its needle point into the diseased parts comprises: a needle body which consists of an optical fiber for transmitting light from a light source over nearly the entire length of the needle, and a needle point attached to the front end of the optical fiber; and a means such as a light collecting lens for applying light from the light source onto the end surface of the optical fiber so that the light can be transmitted through the optical fiber. The needle point inserted into the affected part of the body collects light from the light source and radiate light or heat against the affected part, producing improved remedial effects.

13 Claims, 1 Drawing Sheet

OPTICAL TRANSMISSION TYPE ACUPUNCTURE NEEDLE

This is a continuation of application Ser. No. 07/800,097, filed Nov. 29, 1991, now abandoned.

BACKGROUND OF THE INVENTION

The present invention relates to an acupuncture needle for treating diseased parts of a human body by inserting it into the affected parts and applying light, with meaning a light wave and an electromagnetic wave in the present invention, or heat to the needle to enhance the curative effect, and more particularly to an optical transmission type acupuncture needle which employs an optical transmission member such as optical fibers in a needle body of such an acupuncture needle.

In recent years, special attention is being focused on an acupuncture or an Oriental therapy, because many people suffer from mental stresses and fatigues resulting from an increased diversity of social environments and many hours of work at display terminals. A sports boom and an increasing number of aged people have also contributed to bringing acupuncture into wide use.

The needles for acupuncture currently available consist generally of a needle body having a needle point to be inserted into the affected part of a patient's body, and a needle holder that encloses and end portion of the needle body opposite to the needle point.

FIG. 1 shows the outline of one example of a conventional acupuncture needle drawn almost to the actual size.

In FIG. 1, reference numeral 1A represents a needle body, which is often made of stainless steel but is also made of other materials such as gold, silver and platinum. Designated 2A is a needle holder that encloses the rear portion of the needle body 1A opposite to the needle point. The needle holder 2A can be formed of various kinds of material and have many designs. The needle holder 2A has a function of preventing the needle body 1A from advancing excessively into the body and also serves as an operating handle for manipulating the needles. There are various kinds of needles—a twist needle (driven into the affected part of the body by being twisted), a strike needle (driven into the body by being tapped lightly), and a tube needle (that uses a tube for introducing the needle).

The acupuncture technique is designed to vitalize the physiological action such as that of the sympathetic nerve by accurately giving stimulations to what is generally called effective points in the body although the method of applying the acupuncture technique (method of inserting the needle) varies depending on the symptoms and the locations of diseased parts.

There are two kinds of acupuncture techniques: one involves sticking a needle into a diseased part or an effective point separate from the diseased part; and another involves sticking the needle into an effective point and also burning moxa at the effective point. It is considered that the application of heat to the diseased part is effective in curing. In the description that follows, the portions of the body where the needles are stuck are referred to generally as diseased parts.

A heating needle, one of acupuncture needles that have been developed, has a resistance heating body at the needle point, which is heated by passing an electric current through it. This needle is complex in structure and expensive and has a drawback of causing side effects due to heat radiating from the entire needle, and therefore is not practical for use with acupuncture.

A so-called optical therapy is being practiced in which light is applied to the diseased parts. For such a therapy, infrared rays, visible light and laser beam are used depending on the symptoms.

In recent years, efforts have been made to develop technologies to apply optics to medicine. Among such known technologies are a laser scalpel and a laser coagulating apparatus making use of a carbon dioxide gas laser.

Measuring systems have been developed that use a combination of optical sensors and optical fibers and form optical circuits between a light source and the detector.

As mentioned above, application of heat or light to the diseased parts of the body is attracting attention of medical researchers for its positive physiological effects although the application means differ depending on the symptoms. With conventional acupuncture which simply sticks a needle to the diseased part, however, the heat application is not expected to provide a desired curing effect.

With another method of acupuncture that involves sticking a needle into the diseased part and burning moxa to apply heat to the affected part, since the heating needle radiates heat from the entire needle body as described earlier, portions of the body other than the diseased parts are undesirably heated, making it difficult to properly apply heat to only the diseased parts.

Further, with the conventional light radiating therapy, while it is easy to apply light onto the surface of the diseased part, the diseased part itself in the body, a target of the acupuncture treatment, cannot be radiated with light without cutting into and exposing the affected part. In other words, heat and light are not applied directly to the affected parts within the body.

SUMMARY OF THE INVENTION

This invention solves the above-mentioned problems experienced with the conventional techniques and its objective is to provide an optical fiber acupuncture needle which is simple in construction and can collect and apply light and heat to localized diseased parts within a patient's body—which cannot be radiated with light or heated by the conventional metallic needles—so as to enhance the remedial effects by the application of light and heat.

To achieve the above objective, a first basic construction of the optical transmission type acupuncture needle according to this invention comprises: a needle body having a needle point to be stuck into a diseased part in a patient's body, said needle body being formed at least partly of an optical transmission member; and a needle holder provided at an end portion of the needle body opposite to the needle point.

A second construction of the optical transmission type acupuncture needle according to this invention that achieves the above objective comprises: a needle body having a needle point to be stuck into a diseased part in a patient's body, said needle body being formed at least partly of an optical transmission member; a needle holder provided at an end portion of the needle body opposite to the needle point; and a light collecting lens provided to the end of the needle body opposite to the needle point in such a way that it is in contact with the end of the light transmission member.

DESCRIPTION OF THE PREFERRED EMBODIMENTS

Figure 1:
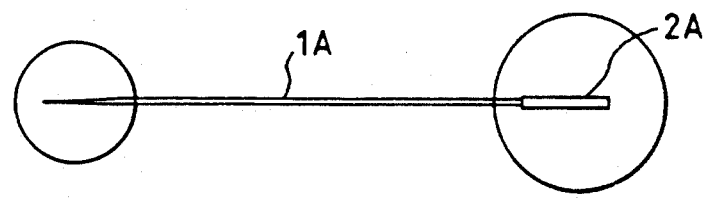
FIG. 1 is an outline view of one example of a conventional acupuncture needle.

In detail, the optical transmission type acupuncture needle of this invention comprises: a needle body which consists of an optical fiber made up of an optical transmission core and a clad for transmitting light from a light source over nearly the entire length of the needle, and a needle point attached to the front end of the optical fiber; and a convex lens to introduce light from the light source onto the end surface of the optical fiber so that the light is transmitted through the optical fiber and converged into the needle point.

The action of the above acupuncture needle will be explained below by referring to FIG. 2.

The needle body 1 which extends over the entire length of the acupuncture needle is made of an optical fiber and has a transparent needle point 1c at the front end and a convex lens 3 bonded to the other end for converging light. The light from a light source passes through the convex lens 3 and enters the optical fiber through the end surface 2a of the fiber. The light is repetitively full-reflected at the boundary surface as it travels through the core 1a and is converged into the transparent needle point 1c.

The needle point embedded in the body of a patient collects light in a localized portion in the body and, depending on the characteristic of the light source 10, can increase the temperature of or radiate light onto the affected part in the body. In this way, the diseased part is appropriately stimulated by heat and/or light to promote curing by stimulated physiological action.

One embodiment of the optical transmission type acupuncture needle according to this invention will be described by referring to FIG. 2.

Figure 2:
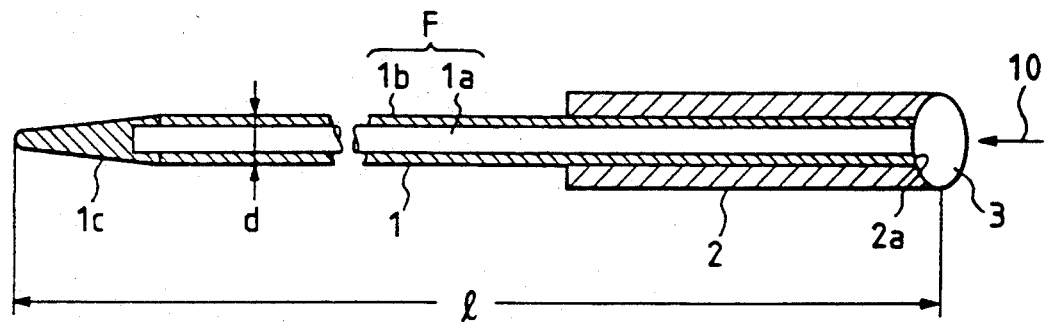
FIG. 2 is an enlarged cross section of a optical fiber acupuncture needle as one embodiment of this invention.

FIG. 2 is an enlarged cross section of an optical fiber acupuncture needle of this embodiment.

In FIG. 2, denoted 1 is a needle body to be inserted into the affected portion of a patient's body. The needle body 1 is made of a light transmitting member such as an optical fiber F, except for a needle point 1c. The optical fiber F consists of a core 1a for transmitting light (not shown) from a light source 10 and a cladding 1b that encloses the core 1a. The optical fiber F has a transparent needle point 1c bonded to one end thereof and a light collecting lens 3 bonded to the other end, which is formed curved to accommodate the lens 3.

Designated 2 is a needle holder that encloses the opposite portion of the needle body 1 to the needle point 1c. The needle holder 2 has the similar function as that of the prior art and has a curved portion 2a formed at the end, to which the light collecting lens is bonded.

Denoted by numeral 3 is a transparent convex lens for collecting light which is fixed to the end of the optical fiber F and to the end of the needle holder 2 opposite to the needle point.

The optical fiber acupuncture needle shown in FIG. 2 will be described in more detail.

Various types of optical fiber are available, such as quartz fiber, multicomponent glass fiber and plastic fiber. It is preferred to use the quartz fiber because it has the least transmission loss among these optical fibers. The quartz optical fiber contains a quartz ($SiO_2$) as a major component in the core 1a with a germanium oxide ($GeO_2$) and other components added to increase the refractive index. The cladding 1b contains a boron oxide ($B_2O_3$) to reduce the refractive index. The cladding 1b may be formed of synthetic resin.

The needle point 1c requires a sufficient strength to be inserted smoothly into the affected part. To avoid stress concentration at the tip, the needle point has the tip rounded with a radius of the order of microns. The material of the needle point is preferably a transparent quartz that can transmit light.

The needle body is made to various sizes with the diameter d ranging from 0.1 mm to 0.5 mm and the whole length l ranging from 50 mm to 300 mm so that an appropriate needle size can be chosen according to the symptoms and the locations of diseased parts.

The convex lens 3 is made of either transparent glass or synthetic resin.

The light source may include, for example, visible light, infrared rays and laser beam, and an appropriate light can be selected according to the symptoms and the location of diseased part.

Now, we will explain about the operation and action of the optical fiber acupuncture needle described above.

The optical fiber acupuncture needle can be manipulated by an acupuncturist in much the same way as he would the conventional acupuncture needle in sticking it in the so-called effective points.

The light from the light source, for example, visible light rays, passes through the convex lens 3 at the end of the needle holder and enters the end surface of the optical fiber F. The rays of light travel through the core 1a of the optical fiber F while being repetitively full-reflected by the boundary surface between the core 1a and the cladding 1b until they reach the transparent needle point 1c. That is, the optical fiber F transmits light from the light source to the needle point 1c without a loss. In other words, the light energy from the light source is also carried through the optical fiber F without any dissipation to the outside and collected to the needle point 1c, from which the light energy is radiated against the diseased part. The light may also be applied as heat energy to heat the diseased part.

The temperature of the needle point 1c is adjusted to an appropriate value according to the object of the treatment by selecting a desired light source.

In this way, the diseased part in the body is treated with heat and light to stimulate physiological action for improved remedial effects.

This embodiment has the following advantages.

(1) In addition to the healing effect provided by the conventional acupuncture needle, this optical fiber needle also offers a direct treatment of the affected part with the light collected to the needle point of the acupuncture needle embedded in the diseased part of the body.

(2) Similarly, the optical fiber needle offers a direct heat therapy of the affected part with the light collected to the needle point of the acupuncture needle embedded in the affected part of the body.

(3) The optical fiber needle further applies light and heat directly to the diseased part in the body, which has not been possible with the conventional metallic acupuncture needle.

(4) Unlike conventional complex medical equipment using optics such as heating needles and laser scalpels, the optical fiber needle is simple in construction and inexpensive and can be handled in the same way as the conventional metallic acupuncture needle.

Next, another embodiment of this invention will be described by referring to FIG. 3.

Figure 3:
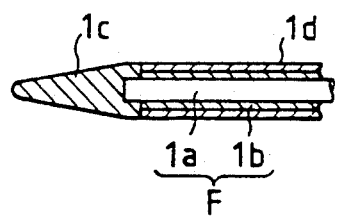
FIG. 3 is an enlarged cross section of an essential portion of the optical fiber acupuncture needle as another embodiment of the invention.

FIG. 3 shows an enlarged view of an essential portion of the optical fiber acupuncture needle as another embodiment of this invention. The figure shows the front part of the needle body. The needle holder and convex lens are similar in construction to those of FIG. 2. The parts identical to those of FIG. 2 are assigned like reference numerals and their explanations omitted.

What differs from the previous embodiment of FIG. 2 is the construction of the needle body, in which the optical fiber F is covered with a cladding member 1d in FIG. 3. The cladding member 1d need only have a sufficient strength to protect the optical fiber f and to permit acupuncture treatment.

While in the above embodiments the light collecting convex lens is shown attached to the end of the optical fiber acupuncture needle opposite to the needle point, it is possible to transmit light from the light source through he optical fiber needle to the needle point even if the convex lens is not provided and still produce reasonable light and heat collecting effects. It is needless to say that it is desirable to provide the light collecting lens.

Although in the above embodiments the needle point is made of transparent quartz, it is not limited to this material alone but may use metals with good heat conductivity (non-light-permeable material). This material is effective when priority is given to heat over light in the treatment.

As described in the foregoing, this invention provides an optical transmission type acupuncture needle which is simple in construction and which can collect and radiate light and heat to a desired affected part within a patient's body—to which the conventional metallic acupuncture needle cannot apply light or heat—to enhance the remedial effects on the diseased part in the body.

What is claimed is:

1. An optical transmission type acupuncture needle comprising:
   an elongated needle body having a needle point at one end portion thereof configured to be stuck into a diseased part in a patient's body and a needle holder provided at another end portion of the needle body opposite to the needle point, said needle body being formed between the end portions of the elongated needle body at least partly of an optical transmission member configured such that light travelling through the optical transmission member is repetitively full reflected at an outer peripheral boundary surface of the needle body so as to converge into the needle point.

2. An optical transmission type acupuncture needle as claimed in claim 1, wherein said needle point is so shaped that a tip thereof is founded with a radius of an order of microns.

3. An optical transmission type acupuncture needle as claimed in claim 2, wherein
   said needle body being formed of an optical fiber portion over nearly an entire length thereof, said optical fiber portion being made up of a light transmission core portion for carrying light from a light source and a clad portion, said needle point being provided to a front end of the optical fiber portion;
   a needle holder provided at an end portion of the needle body opposite to the needle point; and
   a convex lens for passing light from the light source onto an end surface of the optical fiber portion so that the light is transmitted through the optical fiber and thereby collected at the needle point.

4. An optical transmission type acupuncture needle, comprising:
   a needle body having a needle point configured to be stuck into a diseased part in a patient's body, said needle body being formed at least partially of an optical transmission member;
   a needle holder provided at an end portion of the needle body opposite to the needle point; and
   a light collecting lens provided at an end of the needle body opposite to the needle point at an end of the transmission member.

5. An optical transmission type acupuncture needle, comprising:
   a needle body having a needle point configured to be stuck into a diseased part in a patient's body, said needle body being formed of an optical fiber portion over substantially an entire length thereof, said optical fiber portion including a light transmission core portion for carrying light from a light source and a cladding portion, said needle point being provided to a front end of the optical fiber portion;
   a needle holder provided at an end portion of the needle body opposite to the needle point; and
   a convex lens for passing light from a light source onto an end surface of the optical fiber portion so that the light is transmitted through the optical fiber portion and thereby collected at the needle point.

6. An optical transmission type acupuncture needle as claimed in claim 5, wherein said needle body is an optical fiber covered over an outer circumferential surface thereof with a cladding member.

7. An optical transmission type acupuncture needle, comprising:
   a needle body having a needle point formed of a light-permeable member configured to be stuck into a diseased part in a patient's body, said needle body being formed at least partly of an optical transmission member configured such that light travelling through the optical transmission member is repetitively full reflected at an outer peripheral boundary of the needle body so as to converge into the needle point; and
   a needle holder provided at an end portion of the needle body opposite the needle point.

8. An optical transmission type acupuncture needle as claimed in claim 7, further comprising:
   a light collecting lens provided at the end portion of the needle body opposite to the needle point in such a way that it is in contact with an end of the optical transmission member.

9. An optical transmission type acupuncture needle, comprising:
   a needle body having a needle point formed of a non-light permeable member configured to be stuck into a diseased part in a patient's body, said needle body being formed at least partly of an optical transmission member configured such that light travelling through the optical transmission member is repetitively full reflected at an outer peripheral boundary of the needle body so as to converge into the needle point; and a needle holder provided at an end portion of the needle body opposite the needle point.

10. An optical transmission type acupuncture needle as claimed in claim 9, wherein the optical transmission member is formed of an optical fiber portion over nearly an entire length of said needle body, said optical fiber portion being made up of a light transmission core portion for carrying light from a light source and a clad portion, said needle point being provided to a front end of the optical fiber portion; and further comprising a convex lens for passing light from the light source onto an end surface of the optical fiber portion so that the light is transmitted through the optical fiber and thereby collected at the needle point.

11. An optical transmission type acupuncture needle as claimed in claim 9, further comprising:

a light collecting lens provided at an end of the needle body opposite to the needle point in such a way that it is in contact with an end of the light transmission member.

12. An optical transmission type acupuncture needle as claimed in claim 9, wherein said optical fiber portion is formed over nearly an entire length of said needle body, said optical fiber portion being made up of a light transmission core portion for carrying light from a light source and a clad portion, said needle point being provided to a front end of the optical fiber portion;

a needle holder provided at an end portion of the needle body opposite to the needle point; and a convex lens for passing light from the light source onto an end surface of the optical fiber portion so that the light is transmitted through the optical fiber and thereby collected at the needle point.

13. An optical transmission type acupuncture needle, comprising:

a needle body having a needle point which is so shaped that a tip thereof has a radius on the order of microns to be stuck into a diseased part in a patient's body, said needle body being formed at least partly of an optical transmission member;

a needle holder provided at an end portion of the needle body opposite to the needle point; and a light collecting lens provided at the end of the needle body opposite to the needle point such that it is in contact with at end of the transmission member.

* * * * *